United States Patent
Tugendreich et al.

[19]

[11] Patent Number: 5,971,996
[45] Date of Patent: Oct. 26, 1999

[54] UTERINE EVACUATOR

[75] Inventors: Daniel Tugendreich, Givatayim;
Ben-Rafael Zion, Hasharon, both of Israel

[73] Assignee: Scientific G Ltd., Haifa, Israel

[21] Appl. No.: 09/021,299

[22] Filed: Feb. 10, 1998

[51] Int. Cl.⁶ ................................................. A61B 17/42
[52] U.S. Cl. .......................................... 606/119; 128/898
[58] Field of Search .................................. 606/119, 123, 606/193, 1; 128/898

[56] References Cited

U.S. PATENT DOCUMENTS

| | | | |
|---|---|---|---|
| 4,430,076 | 2/1984 | Harris | 606/119 |
| 5,624,399 | 4/1997 | Ackerman | 606/119 |
| 5,746,750 | 5/1998 | Prestel et al. | 606/119 |

*Primary Examiner*—Michael Buiz
*Assistant Examiner*—Kevin Truong
*Attorney, Agent, or Firm*—Mark M. Friedman

[57] ABSTRACT

A system for achieving evacuation of tissue from within the uterine cavity. A rotating Archimedes screw within a narrow cylindrical sheath achieves mechanical tissue extraction. A vacuum source attached to the sheath removes the extracted tissue from the sheath by suction. A fiber-optic system integrated into the sheath allows the procedure to be performed under direct visual guidance. The narrow diameter of the sheath allows for performance of the procedure without the need for cervical dilation.

4 Claims, 4 Drawing Sheets

UTERINE EVACUATOR

FIELD AND BACKGROUND OF THE INVENTION

The present invention relates to the field of Obstetrics and, in particular, it concerns a device for performing evacuation of the contents of the uterine cavity.

It is known that the termination of pregnancy by means of a medically induced abortion is a frequently performed procedure in the practice of Obstetrics and Gynecology. During the first 16 weeks of gestation, this procedure is generally performed by means of a "Dilatation and Curettage" (D+C) procedure. The procedure of D+C entails dilating the uterine cervix to a sufficient diameter as to allow for the passage of a suction tube through the cervix and into the cavity of the uterus. The contents of the uterine cavity (i.e. the embryonic tissue, also known as the "conceptus") is then evacuated by means of vacuum extraction.

As the viscosity of both uterine secretions and embryonic tissue increases with gestation, progressively larger suction tubes are required for the performance of vacuum extraction in more advanced pregnancies. If a suction tube of too narrow diameter is used, the tube will become blocked, and the conceptus will not be successfully extracted. In general, it is necessary to use a tube whose external diameter in millimeters is equal to the number of weeks of gestation of the conceptus. Thus, a D+C performed at 8 weeks of gestation typically requires the use of an 8 millimeter external diameter suction tube, while a D+C performed at 12 weeks requires that a 12 millimeter tube be used. As the suction tube has to traverse the cervical canal prior to reaching the uterine cavity, predilation of the cervix to the diameter of the suction tube to be used must be performed, prior to introducing the tube. This is typically achieved by means of the insertion and removal of Hegar dilators of progressively larger diameter. In addition, particularly in primiparous patients, the cervix is often "ripened" with sea-weed based pharmaceuticals for several days prior to performance of the D+C; so as to facilitate easier dilation of the cervix.

Performance of induced abortion by means of this standard method of D+C, however, suffers from several deficiencies:

1. It is necessary to dilate the cervix, possibly up to a diameter of 16 millimeters. This invasive process is intrinsically traumatic and painful, and may introduce infection.
2. As the process of cervical dilation is painful, it is necessary to administer general anesthesia to the patient. As such, an anesthesiologist must be in attendance at all D+C procedures, and the patient is exposed to the risks and complications of general anesthesia.
3. It may be necessary to hospitalize the patient, both for the purpose of pre-dilation cervical ripening, and for the purpose of post-anesthesia follow up. In its 1996 report, the CDC Center for Disease Control and Prevention reported an 11% hospitalization rate for purposes of performing D+C procedures.
4. The positioning of the tip of the suction tube within the uterine cavity is performed in a blind manner, or under limited external ultrasound guidance. As such, there is a significant incidence of complications (approximately 5%) such as failure to extract the entire conceptus (necessitating a repeat procedure), perforation of the uterus, creation of a false track into the uterus through the cervix, and damage to the uterus resulting in sterility.
5. As ultrasound visualization of the conceptus in a gravid uterus is only possible after 45 days of gestation, it is not possible to perform D+C under ultrasound guidance prior to this date.
6. Due to the blind nature of the procedure, it is necessary for an obstetrician to undergo a lengthy period of training to acquire sufficient skill and experience to be able to perform a D+C safely and successfully.

Alternative devices for achieving tissue extraction with the aid of suction are known in other medical sub-disciplines, particularly in the field of orthopedic surgery. Such devices combine a suction catheter with a mechanism, such as a moving blade, for detaching the tissue to be extracted from its surrounding tissue. Such devices, however, are designed to extract hard tissues, such as bone, under direct visualization, and thus are not suitable for use on soft tissues within the uterine cavity, for the following reasons:

1. The blades of such devices are exposed, and may cause damage to the uterus.
2. Such devices remove the detached tissue by suction only, and thus may become blocked by viscous embryonic tissue or secretions.
3. Performance of a D+C using such a device would have to be done either as a blind procedure (which would be particularly dangerous due to the exposed blades of the device), or under endoscopic guidance (necessitating the introduction of a fiber-optic instrument into the uterine cavity, in addition to the tissue extraction device).

There is therefore a need for a device and method for extracting embryonic tissue from the uterus under direct visualization without the need for extensive cervical dilation, and without the need to introduce a second, fiberoptic, instrument into the uterus.

SUMMARY OF THE INVENTION

The present invention is a uterine evacuator, for the performance of D+C procedures, which incorporates a fiber-optic imaging system for guidance, and which achieves tissue evacuation mechanically by means of an Archimedes screw encased within a cylindrical sheath.

The sheath is inserted through the cervical canal into the uterine cavity, and an opening at its tip is approximated to the tissue to be extracted (the conceptus). A fiberscope integrated into the sheath allows for the direct visualization of the tip of the sheath, and its guidance to the target tissue in real time. Rotation of the Archimedes screw within the sheath mechanically draws the tissue to be extracted into the sheath, and transports it to an exit hole at the opposite end of the sheath. The sheath itself prevents surrounding uterine tissue from being damaged by the rotating blades of the Archimedes screw. A vacuum system attached to the exit hole removes the tissue from the sheath, and generates a vacuum within the sheath which aids the process of tissue extraction. The sheath, and its contained components (the Archimedes screw, the fiber-optic fibers, and a fluid flushing system for cleansing the lens of the fiberscope), constitute a disposable unit which is used for one procedure only, and which is reversibly attachable to a motor (which drives the Archimedes screw), a fiberscope viewing mechanism, a fluid flushing mechanism, and a suction device.

As the rotating Archimedes screw is capable of mechanically transporting thick, viscous tissue and secretions without becoming blocked, a sheath of extremely narrow external diameter (4 mm) can be used for D+C procedures being performed both at early and at advanced stages of gestation. It is this narrow diameter of the sheath, in contrast to other extant systems for performing D+C procedures, which facilitates the integration of optical fibers and a lens flushing system into the sheath, while still maintaining a narrow total external diameter (6 mm in its widest dimension). Introduction of a sheath of this cross-sectional dimension into the uterus can be achieved without the need for cervical predilation by means of Hegar dilators. The need for general anesthesia and hospitalization, and the possibility of cervical trauma or infection is thus minimized. Furthermore, as direct visualization of both the tip of the device and the uterine/cervical tissue is achieved through the integrated fiberscope, the likelihood of failure to extract the entire conceptus, perforation of the uterus, creation of a false track into the uterus through the cervix, or damage to the uterus resulting in sterility, is markedly reduced or eliminated. In addition, performance of the procedure under direct visualization through a fiberscope allows for a conceptus which is younger than 45 days of gestation to be identified and removed, and allows for the safe performance of the procedure by an obstetrician who does not yet have extensive experience in performing blind D+C procedures.

According to the teachings of the present invention there is therefore provided, a uterine soft tissue evacuation system, including a sheath; a tissue transporter deployed within the sheath, the tissue transporter being operative to rotationally transport soft tissue along an axis of rotation of the tissue transporter within the sheath, the axis of rotation being a longitudinal axis of the sheath; a motor, operative to rotate the tissue transporter upon the axis of rotation, and a suction generator, operative to generate a suction force within the sheath for transporting the soft tissue within the sheath and for removing the transported soft tissue from the sheath. A method for evacuating soft tissue from a uterus, including the steps of providing a sheath; directing the sheath to the soft tissue, and rotationally transporting the soft tissue from the uterus along an axis of rotation within the sheath, the axis of rotation being a longitudinal axis of the sheath.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a fiber-optic guided, mechanically driven uterine evacuation system.

The principles and operation of a uterine evacuation system according to the present invention may be better understood with reference to the drawings and the accompanying description.

Figure 1:
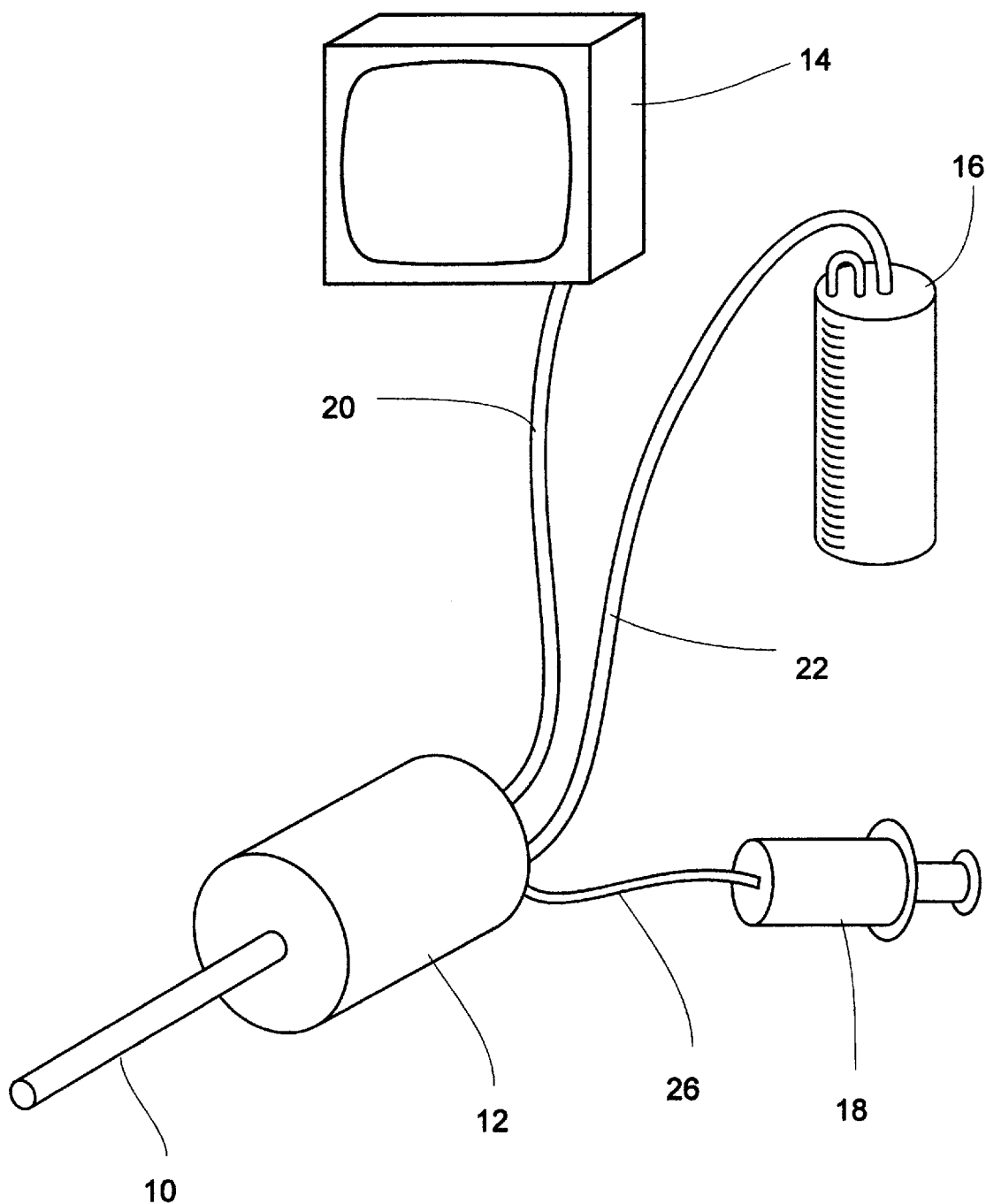
FIG. 1 is a diagram of the overall structure of a uterine evacuation system.

Referring now to the drawings, FIG. 1 is a diagram of the overall structure of a uterine evacuation system. In the preferred embodiment, the system consists of a base unit 12, to which is attached a disposable unit 10, and the following peripheral devices: an optical viewing mechanism 14, a suction generator 16, and a fluid flushing mechanism 18. Disposable unit 10 is the component which is inserted into the uterine cavity of the patient, and is described in detail in FIGS. 2 and 3 below. Optical viewing mechanism 14 is connected to base unit 12 by optical fibers 20. Within base unit 12, optical fibers 20 connect with similar optical fibers (not shown) running in disposable unit 10 and conveying images obtained at the tip of disposable unit 10. Optical fibers 20 convey these images to optical viewing mechanism 14 for display. An example of optical fibers suitable for use as optical fibers 20 are 0.5 mm diameter optical fibers manufactured by Cuda Products Corp. (Jacksonville, Fla.). Any standard fiberoptic viewing device is suitable for use as optical viewing mechanism 14. Suction generator 16 is connected to base unit 12 by means of a hollow tube 22, which conveys a vacuum generated by suction generator 16 to an exit hole (not shown) in disposable unit 10. Any standard suction generating device capable of generating a vacuum pressure in the range of 0–100 mmHg and a flow rate of 0.1–1.5 l/min, such as the vacuum generator manufactured by Ismatec SA (Glattbrugg-Zurich, Austria) is suitable for use as suction generator 16. Fluid flushing mechanism 18 is any mechanism capable of flushing fluid through a second hollow tube 26, for example, a syringe. Second hollow tube 26 connects, in base unit 12, with a similar tube (not shown) running in disposable unit 10.

Figure 2:
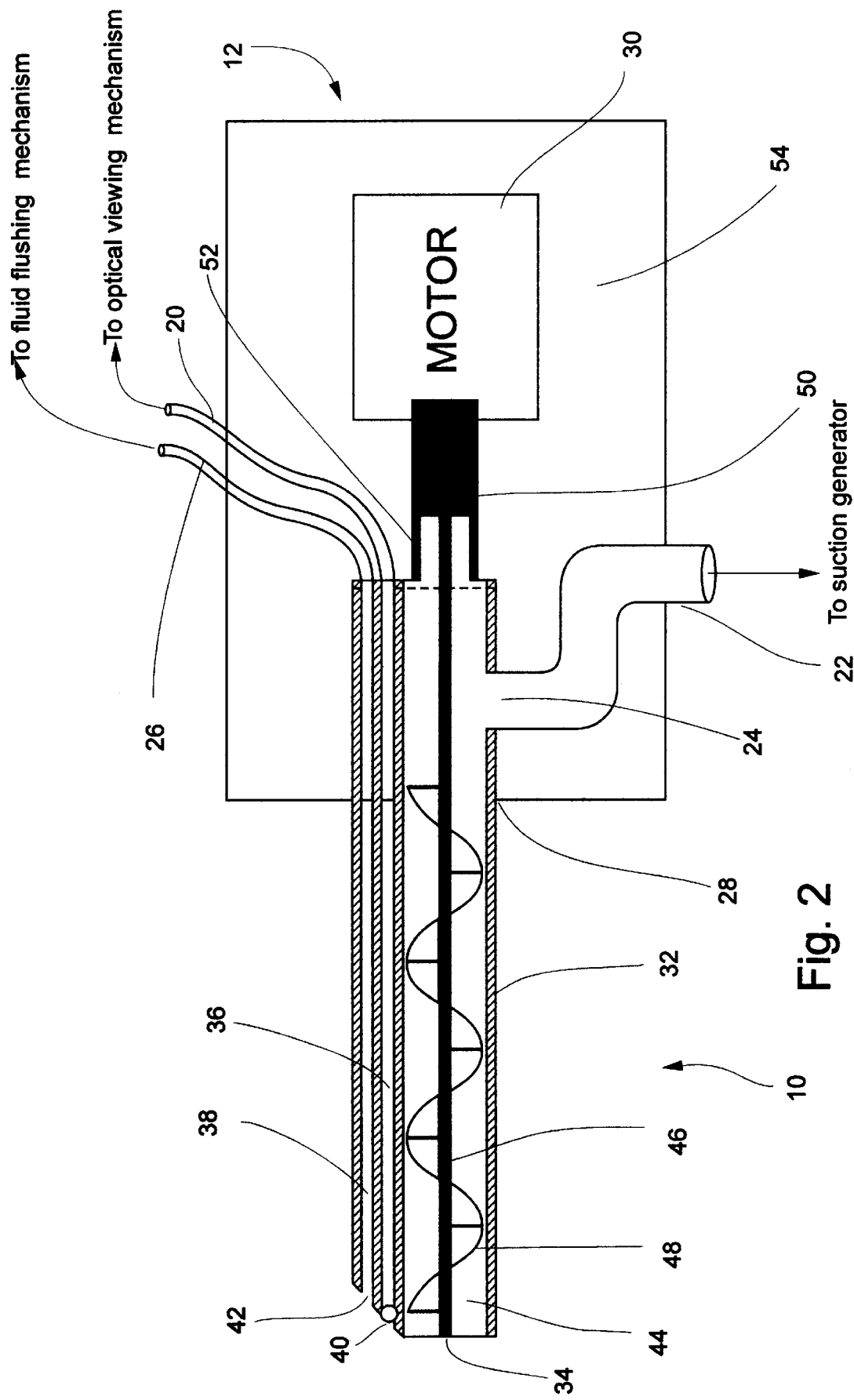
FIG. 2 is a schematic depiction of the base unit and disposable unit.

FIG. 2 is a schematic depiction of base unit 12 and disposable unit 10. Base unit 12 contains a reception port 28 into which disposable unit 10 is inserted. Base unit 12 further contains a motor 30 containing a drive shaft 50. An example of a motor suitable for use in base unit 12 is SMI Model # 0090133039 (Servo Magnetics Inc. Canoga Park, Calif.). Optical fibers 20, hollow tube 22, and second hollow tube 26 enter base unit 12 and terminate at reception port 28. All components of base unit 12 are housed within a casing 54.

Figure 3:
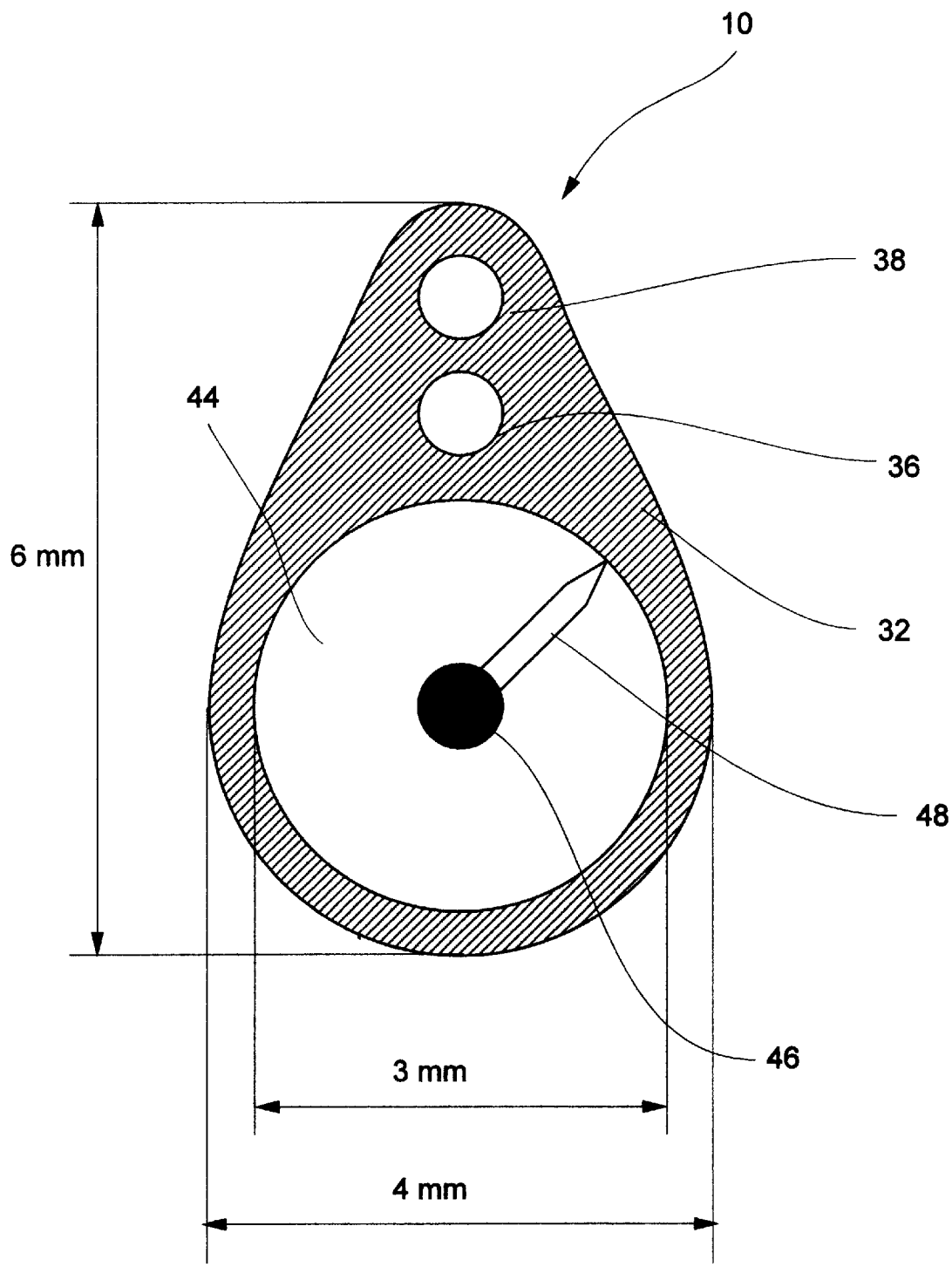
FIG. 3 is a short axis cross-sectional view of the disposable unit.

Disposable unit 10 includes a sheath 32. In the preferred embodiment, sheath 32 is executed from polyethylene or any other FDA approved polymer, and is between 12 and 20 cm in length. An opening 34 into the lumen of sheath 32 is located at the tip of sheath 32. Two channels, a fiber-optic channel 36 containing optical fibers and terminating at a lens 40 at the tip of sheath 32, and a hollow fluid flush channel 38 terminating at a flush opening 42 at the tip of sheath 32, run within the wall of sheath 32 along its the length. Fiber-optic channel 36 is continuous with optical fibers 20 at reception port 28, and fluid flush channel 38 is continuous with second hollow tube 26 at reception port 28. Sheath 32 encloses, within its lumen, a single unit spiral in the form of an Archimedes screw 44, executed from metal. By "Archimedes screw" is meant a broad threaded screw in which the threading is typically inclined at an angle of 30 to 45 degrees to the axis of the central rod of the screw. Archimedes screw 44 includes a center axis rod 46 surrounded by spiral blades 48. Archimedes screw 44 is centered within sheath 32, such that the edges of blades 48 are in continuous contact with the inside surface of the lumen of sheath 32. The tip of center axis rod 46 is located at, but not protruding through, opening 34. The base of center axis rod 46 protrudes beyond sheath 32, is not surrounded by blades 48, and is of a shape, such as a hexagon or a square, matching the shape of a rod reception hole 52 in drive shaft 50. In the preferred embodiment, as shown in FIG. 3, the internal diameter of the lumen of sheath 32, which matches the diameter of blades 48, is 3 mm, the minimum external cross-sectional dimension of sheath 32 is 4 mm, and the maximum external cross-sectional dimension of sheath 32 is 6 mm. An exit hole 24 from the lumen of sheath 32 is located at the base of sheath 32, at a point at which sheath 32 is in contact with reception port 28, and serves to provide continuity between the lumen of sheath 32 and hollow tube 22 leading to suction generator 16.

The system of the current invention functions as follows: The base of disposable unit 10 is inserted into reception port 28 of base unit 12, thereby establishing continuity between fiber-optic channel 36 and optical fibers 20, fluid flush channel 38 and second hollow tube 26, exit hole 24 and hollow tube 22, and center axis rod 46 and rod reception hole 52. The operator inserts sheath 32 into the cervical canal, and advances sheath 32 into the uterine cavity by manipulating base unit 12 while viewing the real time image displayed on optical viewing mechanism 14. This image is captured by lens 40 at the tip of sheath 32, and thus facilitates accurate navigation of sheath 32 through the cervical and uterine cavities. In this manner, damage to the soft tissues, perforation of a viscus or creation of a false track are avoided. If secretions obscure the image captured by lens 40, fluid is flushed via fluid flush channel 38, from fluid flushing mechanism 18, onto lens 40, so as to remove the obscuring secretions. The conceptus within the uterine cavity is identified on optical viewing mechanism 14, and opening 34 of sheath 32 is placed on the conceptus. Motor 30 and suction generator 16 are then activated by the operator, such that Archimedes screw 44 begins to rotate within sheath 32. Both the rotation of Archimedes screw 44 and the vacuum generated by suction generator 16 result in a suction force being generated at opening 34 and within sheath 32. This results in the conceptus tissue being sucked into opening 34, and being mechanically transported up sheath 32 to exit hole 24 by the rotation of Archimedes screw 44. At exit hole 24, the tissue is sucked into hollow tube 22 by the vacuum generated by suction generator 16. Sheath 32 prevents surrounding uterine tissue from being damaged by rotating blades 48. The combination of mechanical transport and suction within sheath 32 allows for the extraction of both gel-like liquid tissue (for example, embryonic tissue during the first few weeks of gestation) as well as solid tissue (for example, a conceptus during more advanced stages of gestation). Solid tissue is broken down into smaller pieces by the rotation of blades 48 of Archimedes screw 44. Upon completion of the procedure, disposable unit 10 is detached from base unit 12 and disposed of.

Figure 4:
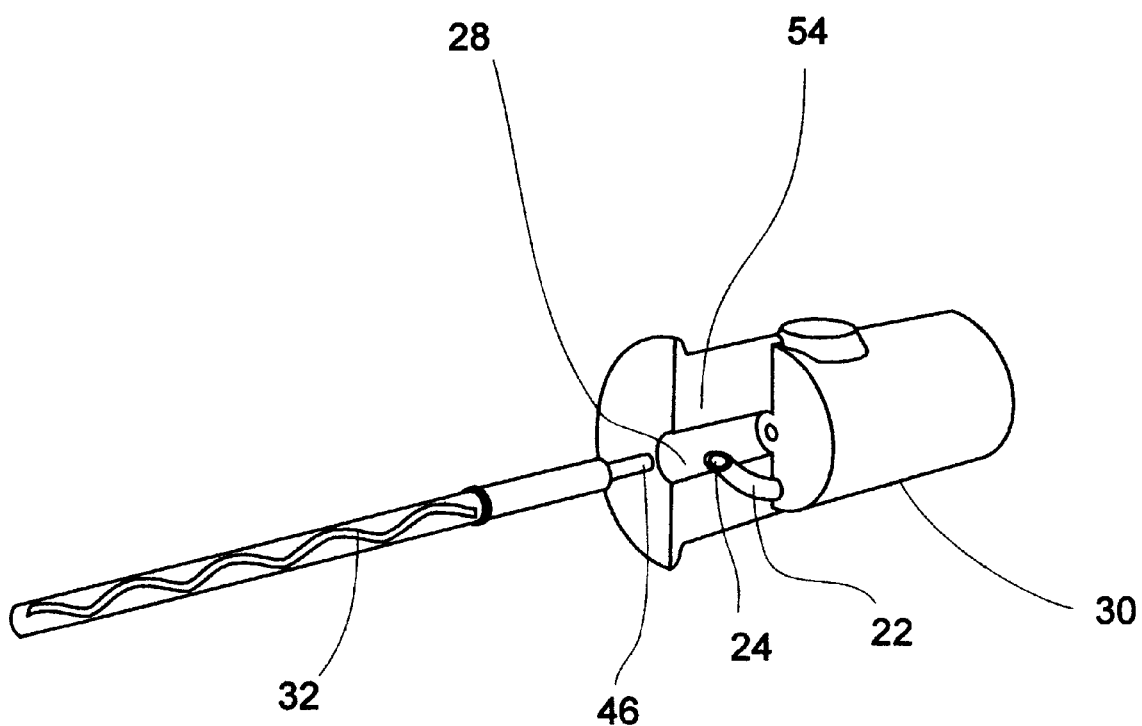
FIG. 4 is a partial cutaway illustration of an alternative embodiment of a uterine evacuation system.

It will be understood that in an alternative embodiment, depicted in a cutaway illustration in FIG. 4, the fiber-optic imaging system and fluid flush mechanism may be omitted from the device. In all other respects, the device is identical to that described above for the preferred embodiment. In this alternative embodiment the D+C procedure is performed blind, as is currently done using standard devices. In this circumstance, the present invention still confers an advantage over standard methods inasmuch as the diameter of the present invention is substantially less than that of standard systems, obviating the need for manual cervical dilation.

What is claimed is:

1. A method for evacuating soft tissue from a uterus, comprising the steps of
   a) providing a sheath;
   b) directing said sheath to the soft tissue, and
   c) rotationally transporting the soft tissue from the uterus along an axis of rotation within said sheath, said axis of rotation being a longitudinal axis of said sheath.

2. The method of claim 1, further comprising the step of
   d) providing a fiber-optic optical sensing system.

3. The method of claim 2, wherein said directing of said sheath is achieved by viewing an environment of said sheath through said fiber optic optical sensing system.

4. The method of claim 1, wherein said rotational transportation of the soft tissue is achieved by a combination of suctioning the soft tissue along said sheath and mechanically transporting the soft tissue along said sheath.

* * * * *